United States Patent [19]

Siddiqi et al.

[11] Patent Number: 4,867,860
[45] Date of Patent: Sep. 19, 1989

[54] METHOD OF MANUFACTURING ION-SELECTIVE ELECTRODES FOR ANALYZING SELECTED IONS IN SOLUTION

[75] Inventors: Iqbal Siddiqi, Geneva; Hans-Rudolf Wuhrmann, Lampenberg, both of Switzerland

[73] Assignee: Hoffmann-La Roche Inc., Nutley, N.J.

[21] Appl. No.: 942,305

[22] Filed: Dec. 16, 1986

[30] Foreign Application Priority Data

Dec. 23, 1985 [CH] Switzerland ............... 5503/85

[51] Int. Cl.$^4$ ............................................. G01N 27/30
[52] U.S. Cl. .................................. 204/418; 204/416; 427/123; 427/124
[58] Field of Search ......... 204/416, 418, 1T; 427/123, 427/124

[56] References Cited

U.S. PATENT DOCUMENTS

| Re. 27,524 | 11/1972 | Nadeau | 195/103.5 |
|---|---|---|---|
| 3,485,723 | 12/1969 | Nadeau | 195/103.5 |
| 3,819,488 | 6/1974 | Rush et al. | 195/103.5 R |
| 3,856,649 | 12/1974 | Genshaw et al. | 204/195 M |
| 4,053,381 | 10/1977 | Hamblen et al. | 204/195 M |
| 4,133,735 | 1/1979 | Afromowitz et al. | 204/195 G |
| 4,171,246 | 10/1979 | Hamblen et al. | 204/195 M |
| 4,184,936 | 1/1980 | Paul et al. | 204/1 T |
| 4,199,411 | 4/1980 | Kim | 204/1 T |
| 4,199,412 | 4/1980 | Battaglia et al. | 204/1 T |
| 4,214,968 | 7/1980 | Battaglia et al. | 204/195 M |
| 4,250,010 | 2/1981 | Kondo et al. | 204/195 M |
| 4,257,862 | 3/1981 | Schnipelsky et al. | 204/195 R |
| 4,272,328 | 6/1981 | Kim et al. | 204/1 T |
| 4,273,639 | 6/1981 | Gottermeier | 204/195 R |
| 4,282,079 | 8/1981 | Chang et al. | 204/1 T |
| 4,303,408 | 12/1981 | Kim et al. | 422/56 |
| 4,314,895 | 2/1982 | Spaziani et al. | 204/418 |
| 4,336,091 | 6/1982 | Gottermeier | 156/244.12 |
| 4,353,983 | 10/1982 | Siddiqi | 435/11 |
| 4,416,735 | 11/1983 | Kissel | 436/74 |
| 4,451,339 | 5/1984 | Kranz et al. | 204/91 |
| 4,454,007 | 6/1984 | Pace | 204/17 |
| 4,466,867 | 8/1984 | Habermann et al. | 204/91 |
| 4,498,739 | 2/1985 | Itaya et al. | 350/357 |
| 4,555,274 | 11/1985 | Kitajima et al. | 148/6.14 R |

FOREIGN PATENT DOCUMENTS

| 29104 | 5/1981 | European Pat. Off. |
|---|---|---|
| 83861 | 7/1983 | European Pat. Off. |
| EP85276 | 8/1983 | European Pat. Off. |
| 1497240 | 8/1967 | France |
| 2146816 | 3/1973 | France |
| 2352300 | 12/1977 | France |
| 2418462 | 9/1979 | France |
| 7113260 | 3/1973 | Netherlands |
| 2102963 | 2/1983 | United Kingdom |
| 2105043 | 3/1983 | United Kingdom |
| 2106253 | 7/1983 | United Kingdom |
| WO80/01081 | 5/1980 | World Int. Prop. O. |

OTHER PUBLICATIONS

James et al., Anal. Chem., 44:856, (1972).
Moore W., Physical Chemistry Prentice Hall Inc., 3rd ed., London, p. 389, (1962).
Kodak, Derwent, 82983Y/47, (1977).
Seshimoto et al., Derwent, 12578K/06, (1983).

*Primary Examiner*—G. L. Kaplan
*Attorney, Agent, or Firm*—Jon S. Saxe; Bernard S. Leon; A. Kate Huffman

[57] ABSTRACT

There is disclosed a process for producing a laminar electrode. The method comprises successive superposition of an insulating support, a conductive layer, a stable-potential internal reference element and an ion-selective diaphragm, all of which are protected by a mask which is impermeable to aqueous solutions. A completely tight seal between the mask and the ion-selective diaphragm is formed by casting the diaphragm in the form of a solution containing a binder which dissolves with and intimately mixes with the mask material.

8 Claims, 2 Drawing Sheets

METHOD OF MANUFACTURING ION-SELECTIVE ELECTRODES FOR ANALYZING SELECTED IONS IN SOLUTION

BACKGROUND

1. Field of the Invention

The invention relates to the manufacture of laminar electrodes having a selectively ion-permeable diaphragm and used for determining specific ion concentration (e.g. $Na^+$, $K^+$, $Mg^{+,}$ $Ca^{+2}$, $Cl^-$, etc.) in aqueous solutions such as a biological fluids.

2. Description

There are already a large number of prior-art electrodes and similar devices for selectively determining ions in aqueous solutions. The electrodes usually comprise an internal electrochemical reference half-cell fixed at a stable potential and adapted, in conjunction with an external reference electrode immersed simultaneously with the measuring electrode in a solution to be analyzed, to form an electrochemical cell of a potential dependent on the presence of a given ion in the solution. As described in the literature, a prior art assembly of this kind comprising two electrodes and a connecting electrolyte and it is described as a "battery". We shall avoid using this term, since a "battery" produces current in contrast to the present cell, which delivers a potential only in order to avoid irreversibility conditions.

The potential of the ion is proportional to the logarithm of the activity of the chosen ion in accordance with NERNST's well known equation $E = E_o \pm K \ln C_i$ where $E_o$ is the standard potential, $K$ is a constant and $C_i$ is the concentration of the ion. The potential is therefore proportional to the conentration of the ion, which can then be deduced by comparison with standard solutions.

For example, Swiss Patent No. 604,167 and U.S. Pat. Nos. 4,214,968; 4,053,381; 4,171,246 (EASTMAN KODAK) describe electrodes in the form of dry multi-laminates comprising, in the following order, an insulating support, a metal electrically conductive layer covered with an insoluble salt of the metal, a part of the layer being used as a terminal for connection to an electrometer, a reference electrolyte and an ion-selective diaphragm for selectively measuring a given ion. The assembly made up of the metal layer, the insoluble salt and the reference electrolyte constitutes the internal reference half-cell at stable potential. Alternatively the assembly can be replaced by a conductive layer covered with a redox system, e.g. the quinone-hydroquinone couple, which system likewise comprises an internal reference cell at stable potential.

The ionically selective diaphragm usually comprises a plasticizer and a hydrophobic matrix containing in dispersion an ionophoric substance, i.e. one used for selectively detecting a given ion to the exclusion of any other ions in the solution to be analyzed. Compare with W. E. MORF et al., Ion-Selective Electrodes in Analytical Chemistry, Vol. I, FRIESER Editor, Plenum Press (1981), pp 221 ff.

U.S. Pat. No. 3,856,649 (MILES) describes an electrode having a similar structure except that the conductive element is filiform instead of laminar and the electrolyte layer is appreciably hydrated.

U.K. Pat. No. 2,106,253 (FUJI) likewise describes an electrode for selectively determining the concentration of ions, the electrode being a laminate comprising an insulating support, a conductive layer covered with an insoluble salt of the metal forming the conductive layer, and a hydrophobic layer of an ion-selective material (ISM) covering the other elements. This document also describes a simplified variant electrode omitting not only the reference electrolyte but also the insoluble salt. In this variant the electrode comprises only the conductive layer covered with ISM material (see also Anal. Chem. 44 (1972), 856).

U.S. Pat. No. 4,454,007 (DUPONT) likewise describes a laminar ion-selective electrode having the following structure: a baseplate of insulating material, a layer of conductive material, a layer comprising powdered carbon dispersed in a dielectric polymer, and finally an ion-selective diaphragm made of material which penetrates with the material in the preceding layer at their junction plane.

In conventional practice, the previously-described electrodes are used as follows. When testing a solution for analysis, a drop thereof is deposited onto the diaphragm, which has selective ion permeability. The drop is also placed in contact with the external reference electrode, e.g. via a salt bridge, the terminals of the ion-selective electrode and the reference electrode being connected to a suitable electrometer for reading the potential. In numerous prior-art cases, the external reference electrode may be similar to or identical with the measuring electrode, and the external reference potential can be supplied either by a standard solution deposited simultaneously with the solution to be analyzed (in which case the solutions make contact by diffusion into a porous element situated between the deposition areas) or by a fixed reference element (the salt bridge for example) forming part of the external reference electrode.

In order to locate and fix the position of the drop of solution to be analyzed (and also the drop of standard solution when necessary) the ISM diaphragm is usually covered with a layer of insulating, waterproof material formed with compartments or windows giving access to only that portion of the ISM layer facing the window. This system prevents the drop spreading on the surface of the ISM layer and can also be used for selecting a fixed preset quantity of liquid for measuring, since the capacity of the compartments is kept constant from the electrode to the other.

Electrodes of this kind, however, are capable of producing short-circuits as a result either of inter-layer diffusion of aqueous liquids or if the liquids accidentally come into contact with the edges of the electrodes. Attempts have been made to obviate these defects by various means, e.g. by tightly sealing the edges of the electrodes (GA-A-2 106 253) or by grooving the conductive layer so as to divide it into zones and filling the grooves with ISM material (GA-A-2 121 183).

SUMMARY OF THE INVENTION

The present invention concerns a process for producing a laminar electrode, which electrode avoids the above described short-circuit problem associated with prior art devices. With the electrodes made according to the invention, the risk of short-circuits has been obviated by completely tightly sealing the ion selective (ISM) diaphragm to the impermeable hydrophobic mask covering the electrode. The tight seal between these components completely prevents any inter-layer diffusion of aqueous liquids and, thus, eliminates the risk of short-circuits.

More particularly, the present invention is directed to a method for producing a laminar electrode having an ion-selective diaphragm for determining selected ions in aqueous media, inter alia, in biological fluids. The electrode has a very short response time, very rapid stabilization, a low drift and is storable in air without requiring any pretreatment before use. The electrode includes an electrochemical half-cell having a stable internal reference potential which is disposed on a conductive base layer and adapted, when the diaphragm and an external reference electrode are electrically interconnected by the solution, to measure the potential and consequently the ion concentration of the solution.

The inventive method comprises the forming of a laminate from the following in succession: (a) an insulating support, (b) a conductive base layer, (c) an internal reference half-cell and (d) a waterproof insulating mask which covers the other elements and is formed with at least one aperture or window in which a layer of a solution comprising an organic solvent, an ionophore, a plasticizer and a binder is deposited. The solution is subsequently solidified by evaporation to form the ion-selective diaphragm. In accordance with the inventive process the solvent used for the diaphragm, is also a solvent used in the formation of the mask material. This shared property and resulting solvent welding causes the two components to be intimately compatible so as to ensure a perfectly sealing-tight junction zone between them and eliminate the risk of short-circuits between the electrode layers.

In a preferred embodiment, the internal reference potential half-cell comprises a metal layer covered successively by an insoluble salt of the metal and a dry electrolyte where the anion is identical with that of the insoluble salt and the cation is identical with the ion to be measured. In order to produce the layer of dry electrolyte disposed on the insoluble salt covering the base metal, a homogeneous layer of the electrolyte is deposited on the surface of the insoluble salt and the resulting salt is dehydrated until its moisture content is below 1% by weight.

The electrolyte can be formed at the surface of the insoluble salt by depositing thereon a homogeneous layer of an aqueous solution of the electrolyte. The solvent thereof is evaporated to dryness and the substance is dehydrated by heating to at least about 115° C. In an alternate embodiment. The electrolyte is formed at the surface of the insoluble salt by physical vapour deposition (PVD), inter alia by evaporation in vacuo.

In another embodiment, the internal reference potential half-cell produced by the inventive process comprises a conductive layer covered with a redox system of the system comprises Prussian blue obtained by immersing the conductive layer in a solution of ferric chloride and alkaline ferrocyanide. Ferric ferrocyanide then is precipitated on the conductive layer in contact with the solution. Precipitation can be accelerated and regularized by negatively polarizing the conductive layer relative to the solution.

BRIEF DESCRIPTION OF THE DRAWINGS

The invention will now be described in greater detail with reference to the accompanying drawings in which.

DETAILED DESCRIPTION OF THE PREFERRED EMBODIMENTS

Figure 1:
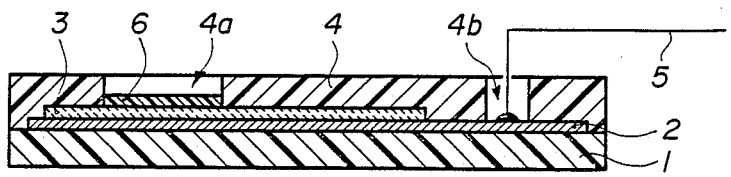
FIG. 1 is a diagrammatic cross-section through an embodiment of an electrode constructed according to the invention.

FIG. 1 shows an electrode comprising the following components sequentially formed as a laminar; an insulating base plate or sheet 1, an electrically conductive layer or base plate 2 co-operating with the next layer, reference element 3 to form a redox system, an internal electrochemical reference cell at stable potential, and finally a mask 4 covering the other above described elements. The mask preferably is made of hydrophobic insulating material and formed with two apertures or windows 4a and 4b. Window 4b is for establishing electric contact (e.g. via a conductor 5) and it thus provides a contact terminal connecting the conductive layer 2 to one terminal of an electrometer (not shown).

The electrode also comprises a diaphragm 6 disposed in compartment or window 4a and in electrical contact with reference element 3. Diaphragm 6 selects specific ions, e.g. K+ ions, and is secured in completely sealing-tight manner to the walls of the mask 4 as a result of inter-diffusion of the (polymer) binder of diaphragm 6 and the material of mask 4. This interpenetration results from the inventive method of manufacture as will be detailed later.

Figure 2:
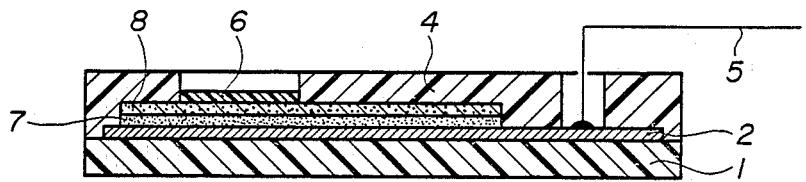
FIG. 2 is a diagram cross-section of another embodiment thereof.

The configuration of the electrode embodiment in FIG. 2 is similar to that in FIG. 1, and consequently like elements are denoted by like reference numbers. This variant, however, differs with regard to the nature of the reference half-cell at stable potential. In the present case, in addition to the conductive metal base 2, the cell comprises a layer 7 of an insoluble salt of the conductive-base metal 2 and a reference electrolyte where the anion is identical with that of the insoluble salt and the cation identical with that which is to be measured in the analyzed substance. In order for example, to determine K+, the conductive base 2 can be silver, the insoluble salt can be a silver halide such as AgCl, and the electrolyte 8 can be a potassium halide, e.g., KCl. In this application, the halides include fluoride, chloride, bromide and iodide.

Figure 3:
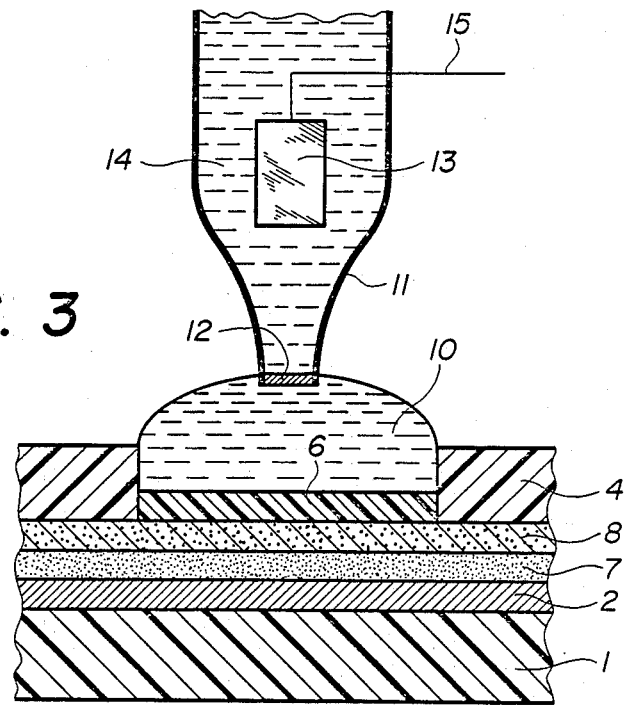
FIG. 3 is a larger-scale diagrammatic representation of a method of measuring ion potential using an external reference electrode.

FIG. 3 illustrates a method of analyzing a solution 10 using the electrode in FIG. 2 (the first variant of FIG. 1 will of course be the same in operation).

To make the analysis, a drop 10 of the solution for analysis is taken and deposited in the compartment 4a formed in mask 4, so that it makes contact with the ion-selective diaphragm 6. Next, contact is made with an electrometer via a coupling means, e.g. a pipette 11 having a porous glass tip 12 and a reference electrode 13 (e.g. a silver plate covered with AgCl and immersed in a reference electrode 14, e.g. KCl N). Contact with the electrometer is made via conductor 5 (see FIG. 2) and also via a conductor 15 connected to the reference electrode 13. Next, the potential of the electrochemical cell formed by the aforementioned elements is measured and, if the internal reference potential (elements 2, 7 and 8) and the concentration of the reference solution 14 are known, it is possible to calculate the concentration of chosen ions in solution 10 by using the NERNST relation (see e.g. "Physical Chemistry" by W. J. Moore, Prentice-Hall, Inc. 3e ed. London 1962, p. 389).

The electrodes according to the invention can be constructed by using any conventional insulating base 1 comprising a sheet, film or plate of for example, a polymer such as PVC, mylar, cellulose acetate, polycarbonates, plexiglass, polystyrene, etc. The nature of the insulating base is not critical provided it does not interfere with the other electrode components, and it can be made from conventional materials and by conventional methods.

The conductive layer 2 can be made from a metal sheet or film, e.g. Fe, Pt, Ag, Cu, Ni, Co, etc., inter alia provided the layer is coated with an insoluble salt 7 of the base metal. Should for example layer 2 be silver, it can comprise a sheet of silver between 10 and 100 µm thick or a silver deposit produced by conventional "electroless" techniques or by vaporization in vacuo or by using a silver paint, containing silver or a silver salt, e.g. Type P-720 or P-750 produced by JOHNSON-MATTHEY, England. An aforementioned silver layer can be coated with an insoluble silver salt, e.g. silver chloride, by oxidation by conventional methods, e.g. chemically or by anodization in the presence of HCl and by conventional methods.

In the case of the electrode shown in FIG. 1, the internal reference-potential element is a conventional redox couple, in which case the conductive layer 2, in addition to a metal as previously described, can comprise other conventional conductive substances such as carbon powder or fibers (in a polymer) or a porous carbon sheet.

The redox reference system, with or without polymer binders, can be a conventional redox system such as quinhydrone or ferrous/ferric couples such as $Fe(CN)_6^{-4}$, $Fe(CN)_6^{-3}$ or cobaltous/cobaltic, e.g. $Co(terpyridyl)_2^{+3}/Co(terpyridyl)_2^{+2}$.

With the inventive process, it unexpectedly has been found possible to use therein Prussian blue. In that case, the system is prepared by immersing the conductive layer 2 in an $FeCl_3$ solution and subsequently in an alkaline ferrocyanide solution. The result is an adhesive layer of Prussian blue between 0.1 and 10 µm thick and exhibiting a potential (on an Fe, Ni, Co or carbon support) which is particularly stable. The following are examples of binders suitable for redox couples: gelatine, polyvinyl alcohol, polyacrylamide, polyvinyl pyrrolidone, etc.

When using a conductive metal layer 2 covered by an insoluble salt 7 (the variant in FIG. 2) it is advantageous to coat it with an electrolyte such as KCl dispersed in a hydrophilic polymer such as gelatine or polyhydroxyacrylic acid. Alternatively, it has been unexpectedly found that use can be made of a layer of electrolyte which is completely dry and without a hydrophilic binder, e.g. KCl, NaCl or another alkali-metal or alkaline earth salt, etc., obtained by complete evaporation and drying of a solution of one of these salts. The possibility of using a dehydrated alkaline salt as the stable-potential reference electrolyte is a surprising and unexpected development, since the resulting electrode rapidly stabilizes and has a very short response time. In this application, the alkali metals include lithium, sodium and potassium. The alkaline earth metals include beryllium, magnesium, calcium, strontium and barium.

The mask 4 covering the electrode can be made of a hydrophobic polymer such as polyvinylchloride (PVC), polyacrylate, polystyrene, polycarbonate, etc. The mask does not require any complicated device for positioning it, since the sealing-tightness of the operating zone of the electrode does not depend on the actual mask over the other components of the laminate, but rather on the uniformity of the material joining the mask 4 to the ion-selective diaphragm 6. For example the mask can be a single sheet of adhesive polymer applied by hot or cold pressure onto the other components of the laminate and intimately following their shape. Alternatively, the conventional "solvent casting" or "solvent welding" technique can be used.

Diaphragm 6 comprises a binder, a plasticizer and an ionophore. The choice of ionophore will depend on the nature of the ions to be determined, e.g. valinomycin for potassium, methyl-monensin for sodium, certain phosphonic esters for calcium, etc. Detailed information on the required ionophores, depending on the chosen type of analysis, will be found among the previous citations, inter alia, U.S. Pat. No. 4,454,007.

The binder for the ionophoric compound can be a polymer such as polyvinyl chloride (PVC), polystyrene, polyacrylates, polycarbonates, polyesters (polyethylene terephthalate), etc. preferably, to obtain optimum compatibility between member 6 and mask 4 (i.e. to ensure solvent weld with maximum sealing-tightness between these components) the polymer chosen for the binder of diaphragm 6 will be identical with the material in the mask, e.g. PVC. Also, in order to assemble the diaphragm, a solution of constituents thereof should be applied in a solvent in which the mask material is also soluble.

The plasticizer used in the diaphragm can be one of the conventional plasticizers such as dimethylphthalate, dioctylphenylphosphonate, dibutylphthalate, tritolylphosphate, dibutylsebacate, etc. Other examples of plasticizers will be found in the citations referred to.

The practical construction of the electrodes by the method according to the invention is simple and follows substantially from the preceding considerations.

Illustratively, the various laminate components are selected and superposed and joined either by simple adhesion or by pressing when cold or hot. For example, in one embodiment of an electrode as per FIG. 1, the method is as follows:

A layer or for example a sheet of silver is deposited onto a plate or sheet of plastic and is anodized in a hydrochloric medium to form an AgCl layer between a few nm and a few µm thick (e.g. 10 nm to 100 µm).

Next, an aqueous solution of KCl at a concentration between e.g. 0.01M and 3.5M is deposited on the AgCl layer and the layer is evaporated and dehydrated until completely dry. The assembly is then covered with an adhesive, for example, PVC mask which has previously been formed with an opening corresponding to window 4a.

The thickness of the mask is of the order of 0.05 to 0.5 mm. Next, a solution of ionophore containing, for example, PVC binder, a plasticizer and a solvent such as THF is deposited in the opening in the mask. The solution is then dried to form a film constituting the diaphragm 6. During this operation, the solvent dissolves part of the walls of the mask with which it is in contact and, after evaporation, forms a completely tight seal between the diaphragm and the walls of opening 4a.

The invention is illustrated by the following nonlimiting examples. Unless otherwise indicated, the examples were carried out as written.

EXAMPLE 1

Electrode with reference cell comprising a dry electrolyte

A. Preparation of a conductive metal base in contact with an insoluble salt of the metal A silver sheet 0.1 mm thick was selected and polished, degreased, cleaned and rinsed by conventional methods (emery No. 600, isopropyl alcohol, distilled water, conc. $NH_4OH$ followed by distilled water). One surface of it was then protected by applying a self-adhesive polyethylene film from 0.2 to 0.5 mm thick. Polyethylene may be replaced by an adhesive PVC or mylar sheet.

An electric contact was formed at the free end of the sheet, after which it was immersed in an electrolytic bath of 0.5M aqueous sulphuric acid and the silver sheet was cathodized under normal conditions: platinum or vitreous carbon counter-electrode, ambient temperature, voltage 4.5 V, duration of treatment 20 min.

The sheet was rinsed with twice-distilled water and placed in a second electrolytic bath of 0.1N aqueous hydrochloric acid and anodized under the following conditions: ambient temperature, current density 0.3 $A/dm^2$, duration 7 minutes. (This and the subsequent operations must be carried out under subdued light to avoid damaging the photosensitive silver chloride).

The sheet was again rinsed and depolarized in the following manner: Two sheets anodized as described were placed in a vessel containing twice-distilled hot water (60°-80° C.) and were electrically short-circuited for 12 hours. After this treatment, the sheets comprised a layer of silver protected on one surface by the plastics sheet and covered on the other surface by a thickness of about 1 to 15 $\mu m$ of AgCl. Manufacture of these reference components was checked by means of a sample, the potential of which was measured in a standard 3M KCl solution using a standard calomel reference counter-electrode. The measured value ($-33$ to $-34$ mV under normal conditions) was correct to within 0.1 mV of the theoretical value. The sheets were dried and kept in darkness until used for manufacturing the electrodes. Note that the anodization treatment can be replaced by oxidation for 1 to 2 minutes at ambient temperature in a solution containing 10.01 g potassium bichromate, 15.4 g KCl and 25 ml of conc. HCl per liter.

B. Manufacture of an electrode which is selective for potassium ions

A $7 \times 15$ mm portion was cut from a sheet of Ag/AgCl prepared as described herein before, and about 20 $\mu l$ of a 3.5M aqueous solution of KCl was deposited over the entire non-protected surface, using a pipette. The water was evaporated from the solution and the plate portion was dried for 8-12 hours at 110° until completely dehydrated. After this period the activated surface was covered with fine KCl crystals (about 5 mg) uniformly distributed over the entire surface. In this treatment, the KCl was not associated with any hydrophilic matrix as in the prior art. Dry KCl layers were also prepared by the same method but using aqueous solutions containing $7 \times 10^{-3}$M and 0.1M KCl. The physical vapour deposition method was also used.

An area of a few $mm^2$ was cleared near the end of the plate portion to serve as a place of electric contact, and a connector (e.g. a connecting wire) was soldered thereto, after which the plate portion was covered with a PVC sheet (mask) formed (see FIG. 2) with an opening or window 4a about 3 to 5 m in diameter giving access to a corresponding area of the active layer of the electrode. Mask 4 was made from a self-adhesive sheet about 0.1 mm thick.

About 20 $\mu l$ of an ISM solution prepared from 6.6 mg of valinomycin (Val); 2.014 mg of bis(2-ethylhexyl)adipate; 2.044 g of high molecular-weight PVC and 20 ml of tetrahydrofuran (THF) was then poured into window 4 through a pipette. The solution was then evaporated, during which time the THF dissolved part of the PVC forming the peripheral walls of the window, resulting in penetration of the PVC binder into the walls of the mask and the ISM membrane. After drying, therefore, the membrane was intimately bonded to the mask walls by a completely water-tight junction zone.

The resulting electrodes were used as follows (see FIG. 3). Using a micropipette, a drop (20-50 $\mu l$) of standard solution (or of solution to be measured) was placed in the compartment 4a in contact with the ISM diaphragm 6. Connector 5 was connected to the terminals of a high-impedance electrometer (differential pre-amplifier, input impedance more than 10-13 ohms, current approximately 2 pA, followed by Digital KEITHLEY-197 multimeter) and also to the external reference electrode, which comprised a sintered-tip micropipette in contact with the drop to be measured and containing a KCl reference solution and a plate of Ag/AgCl.

A comparative test was also made on conventionally constructed electrodes without a dry KCl electrolyte. In the test, the potential was measured every 6 seconds for a total period of 6 minutes. The electrodes in the present example rapidly stabilized and had only a very slight drift, below 0.1 mV/min. The comparison electrodes, on the other hand, had an uncontrollable drift (more than 1 mV/min) which was difficult or impossible to stabilize (see FIG. 3). The results obtained from test solutions of KCl having a concentration of $10^{-2}$ to $10^{-5}$M are shown in the following table. These results relate to electrode previously rinsed in distilled water and then with the solution to be measured at each change of concentration.

| Electrode No. | KCl solution used for the dry KCl layer (M) | Measurement - (mV) Conc. KCl (M) | | | | Linearity range (M) |
|---|---|---|---|---|---|---|
| | | $10^{-5}$ | $10^{-4}$ | $10^{-3}$ | $10^{-2}$ | |
| AK-14 | None (compare.) | 176 | 145 | 99 | 46 | $10^{-2}$–$10^{-4}$ |
| AK-15 | " | 196 | 170 | 124 | 57.2 | $10^{-2}$–$10^{-4}$ |
| AK-16 | " | 162 | 117 | 69 | — | $10^{-3}$–$10^{-5}$ |
| AK-17 | $7 \times 10^{-3}$ | 253 | 220 | 182 | 142 | $10^{-2}$–$10^{-4}$ |
| AK-21 | 0.1 | 265 | 237 | 195 | 162 | $10^{-2}$–$10^{-4}$ |
| AK-22 | 3.5 | 279 | 267 | 232 | 197 | $10^{-2}$–$10^{-4}$ |

Figure 4:
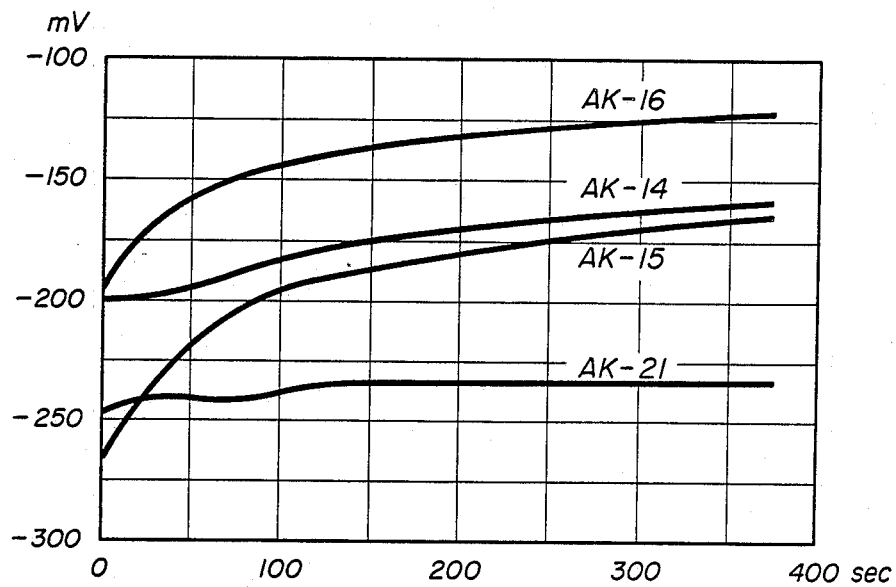
FIG. 4 is a graph showing the variation in potential of virgin electrodes with time.

FIG. 4 is a graph showing the variation in potential of virgin electrodes (including AK-14 to 16 samples for comparison), in dependence on the stabilization time.

EXAMPLE 2

Electrode with reference cell comprising Prussian blue

A sheet of Fe, Ag, Ni, Pt or porous conductive carbon about 0.05 to 0.2 mm thick was selected and immersed for a few minutes in a hot non-ionic detergent, then rinsed a number of times in hot distilled water. After a further rinse in twice-distilled water, the sheet was dried for at least 4 hours at 150° C. The conductive sheet was handled with very great care in order to avoid depositing impurities (metal forceps were used), since Prussian blue is extremely sensitive to impurities.

A solution of 20 mM of $K_4Fe(CN)_6$, analytical grade, was also prepared after being twice recrystallized from thrice-distilled water, which was acidified to 0.01M with HCl. The same method was used with $FeCl_3$ to prepare a corresponding solution of $FeCl_3$ at 0.01M of HCl.

When the two solutions were carefully mixed, the mixture remained in unstable equilibrium; Prussian blue was precipitated subsequently.

One of the conductive sheets was cathodized at 1 $mA/cm^2$ in 1N HCl at 40° C. A Fe or Ni sheet requires 5 minutes treatment whereas Pt takes about 60 minutes; a conductive carbon sheet does not require cathodization.

After this treatment, a sheet was slowly immersed in a freshly prepared mixture of iron chloride solution and ferrocyanide solution, except for a small portion for subsequently forming an electric connection. After five minutes, a layer of Prussian blue formed on the conductive sheet and continued to thicken if the treatment was prolonged. Depending on the desired thickness, the sheet was taken out of the bath after 5 to 20 minutes, carefully rinsed with thrice-distilled water and dried in a desiccator on $P_2O_5$.

Alternatively, deposition of Prussian blue can be accelerated by inserting a second sheet (of platinum) into the mixture and applying a potential between the sheets, the first being negatively polarized so as to obtain a current density of 50 $\mu A/cm^2$. This technique results in more uniform, homogeneous deposition than purely chemical methods. A suitable thick deposit is obtained by passing about 10–15 mCoulombs/$cm^2$ electrode.

After the sheet had thus been covered with Prussian blue, one surface of it was coated with a self-adhesive protective film of polyethylene, PVC or mylar between 0.1 and 0.5 mm thick, after which a portion measuring approximately 7×15 mm was cut out of the sheet. The portion was given an end zone which was not coated with the redox system, and of use for subsequently connecting the electrode to an electrometer.

The sheet portion (except for the contact zone 4b) was then covered with a sheet of PVC (mask) formed (see FIG. 1) with an aperture or window 4a about 3 to 5 mm in diameter, giving access to a corresponding area of active electrode. A shelf-adhesive sheet about 0.1 mm thick was used for mask 4.

Next, about 20 $\mu l$ of an ISM solution was poured into window 4 through a pipette. The solution was prepared from 6.6 mg of valinomycin (Val); 2.013 mg of bis(2-ethylhexyl)adipate; 2.044 g of high molecular weight-PVC and 20 ml of tetrahydrofuran (THF). The solution was then evaporated, during which time the THF dissolved part of the PVC forming the peripheral walls of the window, so that the PVC binder penetrated into the walls of the mask and the ISM diaphragm. After drying, therefore, the diaphragm was intimately bonded to the walls of the mask by a completely sealing-tight junction zone.

The resulting electrodes were used as follows (see FIG. 2). Using a micropipette, a drop (20–50 $\mu l$) of standard solution (or solution to be measured) was deposited in compartment 4a in contact with the ISM diaphragm 6. Connector 5 was connected to the terminals of a high-impedance electrometer (differential preamplifier, input greater than $10^{-3}$ ohms, current approx. 2 pA, then digital KEITHLEY-197 multimeter) and the external reference electrode, which comprised a sintered-tip micropipette in contact with the drop to be measured, containing a reference KCl M solution and a plate of Ag/AgCl. In the test, the potential was measured every 6 seconds for a total of 6 minutes. The electrodes in the present example stabilized quickly and their drift was very small—below 0.1 mV/min. The results obtained on test solutions of KCl at concentrations from $10^{-2}$ to $10^5 M$ are shown in the following Table. These results relate to electrodes which have previously been rinsed in distilled water and then with the solution to be measured, at each change in concentration.

| Electrode No. | Conductive base | Measurement (mV) Conc.Sol.KCl (molarity) | | | | Linearity range (M) |
|---|---|---|---|---|---|---|
| | | $10^{-5}$ | $10^{-4}$ | $10^{-3}$ | $10^{-2}$ | |
| PB-1 | C porous | 361 | 393 | 443 | 497 | $10^{-2}-10^{-4}$ |
| PB-2 | Ni (Fe)* | 128 | 122 | 162 | 201 | $10^{-2}-10^{-4}$ |
| PB-3 | C fibres | 167 | 208 | 254 | 304 | $10^{-2}-10^{-4}$ |

*Nickel-plated iron

Figure 5:
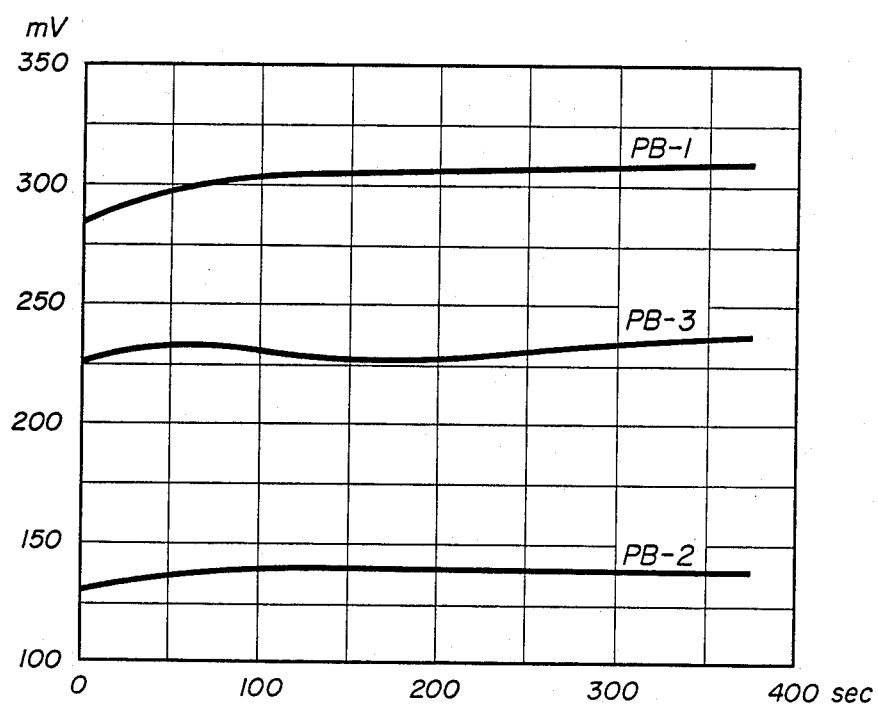
FIG. 5 is a graph similar to FIG. 4 corresponding to other kinds of electrodes.

The stability of the electrodes was very satisfactory; after being stabilized, the potential drift did not exceed ±0.2 mV/min. Stabilization took about 2 minutes (see FIG. 5).

While the invention has been described in conjunction with certain embodiments, it is understood that various modifications and changes may be made without departing from the spirit and scope of the invention.

We claim:

1. A method for producing a laminar electrode for determining selected ion concentration in aqueous media, having an ion-selective diaphragm, an electrochemical half-cell with a stable internal reference potential and a metal conductive base layer, the method comprising:
   (a) forming a laminate from the following in succession: (i) an insulating support, (ii) the conductive base layer, and (iii) the internal reference half-cell;
   (b) covering the laminate with a waterproof insulating mask having at least one aperture;
   (c) depositing in the aperture a layer of a solution comprising an organic solvent, an ionophore, a plasticizer and a binder;
   (d) solidifying the solution by evaporation thereby forming, the ion-selective diaphragm; and
   (e) providing a sealed-tight junction zone between the diaphragm and the mask by the solvent used to form the diaphragm being suitable as a solvent for the mask.

2. The method of claim 1, further comprising forming the internal reference potential half-cell by
   (c) successively covering the base layer by an insoluble salt of the metal and a dry electrolyte where the anion is identical with that of the insoluble salt and the cation is identical with the ion to be measured; and
   (b) depositing a homogeneous layer of the electrolyte on the surface of the insoluble salt and dehydrating the resulting salt until its moisture content is below 1% by weight to produce the layer of dry electrolyte disposed on the insoluble salt covering the base layer.

3. The method of to claim 2, further comprising;

(a) forming the electrolyte at the surface of the insoluble salt by depositing thereon a homogeneous layer of an aqueous solution of the electrolyte, and
(b) evaporating the solvent thereof to dryness and heating the substance to at least about 115° C.

4. The method of claim 2, further comprising forming the electrolyte at the surface of the insoluble salt by physical vapour deposition.

5. The method of claim 4, wherein the physical vapour deposition is provided by evaporation in vacuo.

6. The method of claim 1, in which the internal reference potential half-cell has the conductive base layer covered with a redox system, the system being formed by immersing the conductive layer in a solution of ferric chloride and alkaline ferrocyanide, and precipitating ferric ferrocyanide on the conductive base layer in contact with the ferric chloride and alkaline ferrocyanide solution to obtain thereon a layer of Prussian blue.

7. The method of claim 6, wherein the precipitation is accelerated and regularized by negatively polarizing the conductive base layer relative to the ferric chloride and alkaline ferrocyanide solution.

8. The method of claim 1, wherein the sealed-tight function zone is provided by solvent welding the mask to the diaphragm.

* * * * *